(12) United States Patent
Harris

(10) Patent No.: US 6,729,942 B2
(45) Date of Patent: May 4, 2004

(54) DENTAL ABRASION SYSTEM

(76) Inventor: William H. Harris, 901 NE. 42nd St., Oklahoma City, OK (US) 73105

( * ) Notice: Subject to any disclaimer, the term of this patent is extended or adjusted under 35 U.S.C. 154(b) by 0 days.

(21) Appl. No.: 10/253,975

(22) Filed: Sep. 24, 2002

(65) Prior Publication Data

US 2004/0058627 A1 Mar. 25, 2004

(51) Int. Cl.$^7$ ................................................. B24C 5/00
(52) U.S. Cl. ............................ 451/91; 451/75; 451/89; 451/90; 451/99; 451/101; 451/102; 433/28; 433/80; 433/82; 433/84; 433/85; 433/87; 433/88; 433/89; 433/125
(58) Field of Search ............................. 451/75, 89, 90, 451/91, 99, 101, 102; 433/28, 80, 82, 84, 85, 87, 88, 89, 125

(56) References Cited

U.S. PATENT DOCUMENTS

| | | |
|---|---|---|
| 2,874,470 A | 2/1959 | Richards |
| 3,064,749 A | 11/1962 | Brass |
| 3,972,123 A | 8/1976 | Black |
| 4,174,571 A | 11/1979 | Gallant |
| 4,412,402 A | 11/1983 | Gallant |
| 4,462,803 A | 7/1984 | Landgraf et al. |
| 4,595,365 A | 6/1986 | Edel et al. |
| 4,648,840 A | 3/1987 | Conger, Sr. |
| 4,676,749 A | 6/1987 | Mabille |
| 4,696,644 A | 9/1987 | Goof |
| 4,878,320 A | 11/1989 | Woodson |
| 4,950,160 A | 8/1990 | Karst |
| 4,984,984 A | 1/1991 | Esrock |
| 5,090,904 A | 2/1992 | Bailey |
| 5,094,615 A * | 3/1992 | Bailey .......................... 433/88 |
| 5,123,206 A | 6/1992 | Woodson |
| 5,158,455 A * | 10/1992 | Bailey .......................... 433/88 |
| 5,186,625 A * | 2/1993 | Bailey .......................... 433/88 |
| 5,242,300 A * | 9/1993 | Esrock .......................... 433/80 |
| 5,275,561 A | 1/1994 | Goldsmith |
| 5,336,202 A | 8/1994 | Bailly et al. |
| 5,618,177 A | 4/1997 | Abbott |
| 5,967,779 A | 10/1999 | Brassil et al. |
| 6,039,567 A | 3/2000 | Abbott et al. |
| 6,053,803 A | 4/2000 | Pizzimenti et al. |
| 6,093,021 A | 7/2000 | Rainey |
| 6,106,288 A | 8/2000 | Brassil et al. |
| 6,149,509 A | 11/2000 | Bruns et al. |
| 6,155,824 A | 12/2000 | Kamen et al. |
| 6,186,422 B1 | 2/2001 | Hubner et al. |
| 6,273,789 B1 | 8/2001 | LaSalle et al. |
| 6,309,217 B1 | 10/2001 | Aumuller |

* cited by examiner

Primary Examiner—Joseph J. Hall, III
Assistant Examiner—Shantese McDonald
(74) Attorney, Agent, or Firm—James F. Harvey, III; Derrick W. Harvey

(57) ABSTRACT

The present invention provides a portable dental system for use in areas having inadequate sources of power, either for human or for veterinary dentistry. The system provides one or more handpieces, each driven driven by a pressurized nitrogen gas contained in a portable tank. A water reservoir is also provided for medicated water to be applied to the tooth site. The system has two channels to which either a conventional dental handpiece or an abrasive handpiece can be attached. When two abrasive handpieces are attached, two different abrasive materials may be used by the system, one material for cleaning and one material for cutting or abrading.

23 Claims, 3 Drawing Sheets

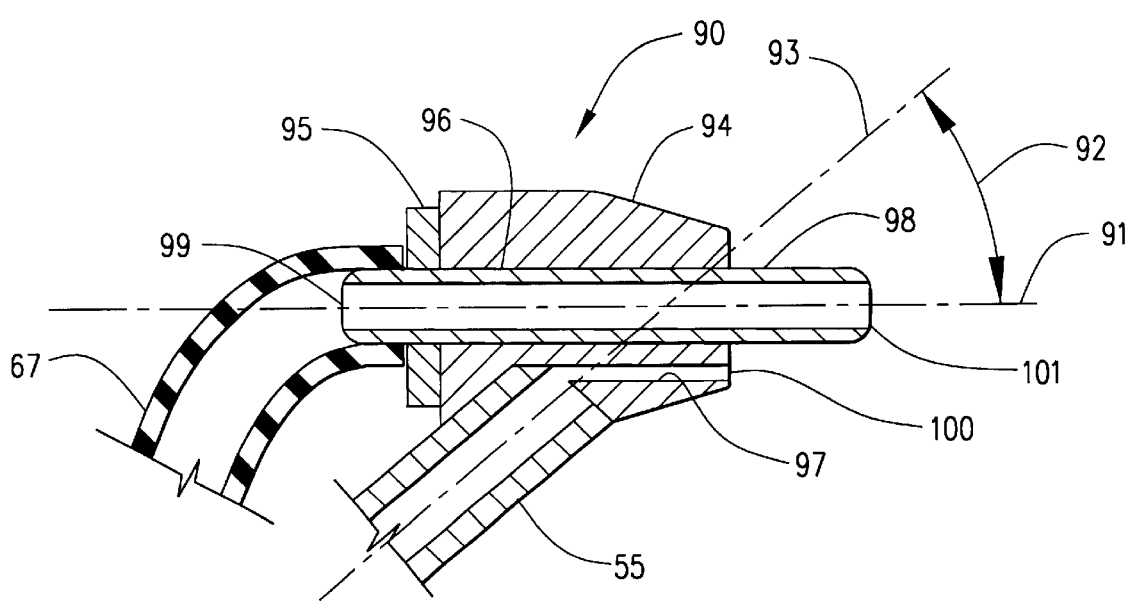
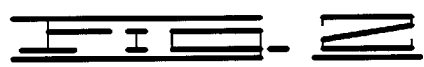
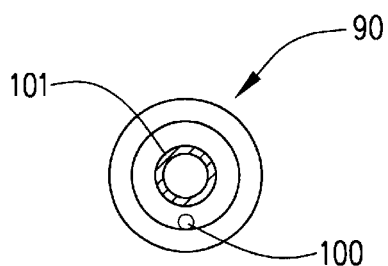
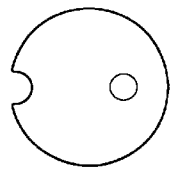
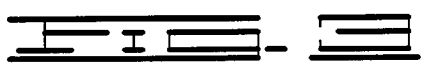

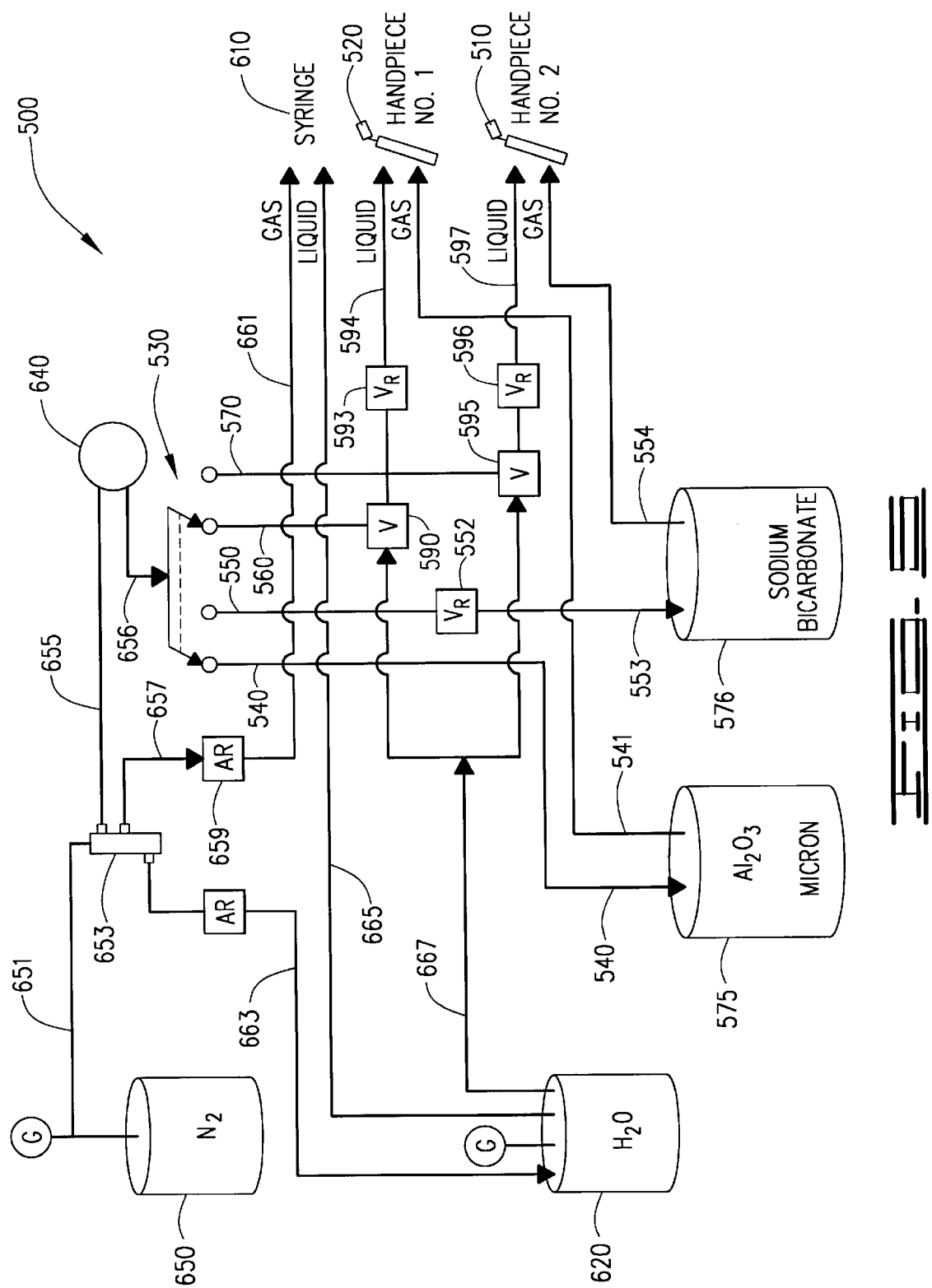

DENTAL ABRASION SYSTEM

BACKGROUND OF THE INVENTION

The present invention relates to the field of dental equipment. More specifically, this invention is concerned with portable dental tools for either cleaning the tooth surface or cutting away or abrading selected portions of the tooth, depending upon the type of abrasive.

Dental hand pieces traditionally are used for cleaning and abrading the surface of teeth through a combination of an abrasive medium and a liquid delivered to the surface of the teeth. Commonly, the hand pieces have a nozzle through which a gas stream, typically air, with powdered abrasive contained therein is delivered to the tooth area. To effectively clean teeth with abrasives, the pressure of the gas delivering the abrasive must be of a substantial strength to remove foreign materials such as plaque, stains, and minor calculus deposits. The liquid, typically a medicated or antiseptic aqueous solution, is used to reduce the plume of rebounding abrasive material and dental material and keep the tooth area free of extraneous material.

The use of abrasives in the area of dentistry has been long known. Abrasives have been used for either removing foreign materials such as plaque, stains, and calculus deposits from the surface of human teeth without damage to the enamel, or cutting away of tooth material comprising caries in preparation for fillings of various types. Abrasive materials employed in the cleaning process have generally been either water soluble compounds such as sodium bicarbonate ($NaHCO_3$) or water insoluble compounds such as aluminum oxide ($Al_2O_3$). The standard abrasive process employs an abrasive-laden gas stream having particles of the abrasive material suspended therein and a liquid at high pressure. The two streams are either combined prior to directing them to the tooth surface or directed separately to the tooth surface where they interact.

For example, U.S. Pat. No. 4,878,320, entitled "Abrasive Feed System", to Woodson, discloses such a system using water-soluble sodium bicarbonate suspended in nitrogen gas for the removal of a covering or coating of a material to be cleaned without damaging the underlying substrate.

However, the use of abrasives within a high pressure system has attendant problems associated with such use. First, the abrasive tends to rapidly abrade the interior of the nozzle directing the abrasive stream to the tooth and the channel through which the abrasive-laden gas travels, necessitating the reworking and replacement of various parts of the handpiece, nozzle arrangement, and the abrasive system in general. This abrading action is particularly problematic for abrasive systems having 90° or other relatively sharp bends in the gas channel, since the abrasive more rapidly wears the interior or the channel at those points of sharp curvature.

Second, channels often clog with precipitate formed in systems that either internally mix abrasive material and water prior to expelling the mixture or else allow a portion of an expelled abrasive-laden gas stream to be drawn back into the water or gas channels. Abrasive systems in general have minute orifices through which the abrasive-laden stream is tightly focused on a selected area of the tooth. The dry abrasive, when combined with a liquid such as water, tends to clog these small orifices. Complicated and detailed arrangements have been proposed to prevent clogging and ensure a self-cleaning aspect to the abrasive system.

Third, portions of the dental system, and the handpiece in particular, must be autoclaved to prevent the spread of bacteria from patient to patient. The handpiece must be disassembled for use in the autoclave so that all parts may be treated. Some parts of the handpiece are not autoclaved since they do not come into direct contact with the mouth area and may be cleaned by using an alcohol wipe.

Fourth, it is often the case that a person using an dental abrasion system is required to use a water-soluble abrasive for cleaning of teeth and then must switch to a water insoluble abrasive to fix a cavity. Most dental abrasion systems are configured for a single handpiece, a single set of gas/liquid channels, and a single abrasive reservoir. The system must be disassembled and cleaned when changing the type of abrasive. This results in loss of time and increased expenditure of effort.

Fifth, the systems and apparatus in current use are all contemplated for use with human operatories and are not suitable for veterinary use such as equine operatories. When such system are configured for veterinary use, they must frequently be taken into areas remote from electrical and water connections, such as pastures or barns where horses are typically found.

A number of systems have been proposed to address and correct these inherent problems. As one example, U.S. Pat. No. 4,984,984 to Esrock, discloses a system that contemplates replaceable nozzle heads as a solution to the stress and maintenance of abrasion delivery. Esrock also addressed issues of cleaning and sterilizing the system when combining water and the abrasive medium.

As can be seen, there is a need for a dental abrasion system having a durable handpiece with longer intervals between maintenance, better resistance to clogging of gas and water channels by the abrasive material, ability to be autoclaved, and flexibility for use with multiple abrasives without undue down time. Furthermore, there is a further need for a portable system that can be adapted for use in areas without a dependable power or water supply. Such a system should be adaptable for veterinary use, in particular, for use with equine stock.

SUMMARY OF THE INVENTION

In one aspect of the invention, a handpiece for use in an abrasion system is provided. The handpiece may be used by an operator to conveniently direct a pressurized abrasive-laden gas stream and a pressurized liquid stream as separate streams to a work area. The handpiece may comprise an elongate handle sized to gripped by a hand of an operator. The handpiece may further comprise a head assembly for attachment to a first end of the handle. The head assembly may have a nozzle protruding a distance from the head assembly for directing the abrasive-laden gas stream emanating from a tip of the nozzle to the work area, and it may also have an orifice directing the pressurized liquid stream to the same work area. A gas channel may be provided to receive the pressurized abrasive-laden gas stream at a second end of the handle and direct the pressurized abrasive-laden gas stream through the handle and the head assembly to exit the nozzle. A liquid channel also may be provided to receive the pressurized liquid stream at the second end of the handle and direct the pressurized liquid stream through the handle and head assembly to exit the orifice.

In another aspect of the invention, an abrasion system provided for the purpose of abrading a work area, the system comprising a a pressurized gas stream, a pressurized liquid stream, and a means for entraining a first abrasive material in the pressurized gas stream to produce an first abrasive-laden gas stream. First and second handpieces are also provided, the first handpiece simultaneously directing the first abrasive-laden gas stream and the pressurized liquid stream to the work area, so that the resulting plume of material emanating from the work area resulting from the first abrasive-laden gas stream is reduced. The second handpiece may be either a handpiece similar to the first handpiece or a dentist's drill powered by the pressurized gas stream.

In yet another aspect of the invention, a mobile abrasion system is provided, the system having a gas tank providing a pressurized gas stream comprised of nitrogen gas and a water tank providing a pressurized liquid stream, the water tank receiving pressure from the pressurized gas stream. A first reservoir containing a first abrasive material is also included, where the first reservoir receives the pressurized gas stream, entrains the first abrasive material within the pressurized gas stream, and provides a first abrasive-laden gas stream. Two handpieces are also provided. The first handpiece receives the first abrasive-laden gas stream and the pressurized liquid stream and delivers the streams to the work area. The second handpiece also receives the pressurized liquid stream. If the second handpiece is for abrasive work, then a second reservoir containing a second abrasive material is also included, where the second reservoir receives the pressurized gas stream, entrains a second abrasive material within the pressurized gas stream, and provides a second abrasive-laden gas stream to the second handpiece, which then delivers both streams to the work area. If the second handpiece is a dentist's drill, then the second handpiece receives the pressurized gas stream to operate the drill. A switch is provided to alternatively enable the first abrasive-laden gas stream and the pressurized liquid stream to flow to the first handpiece and enable the pressurized liquid stream to flow to the second handpiece, wherein the nonselected handpiece is disabled from the streams. The switch will also enable the second abrasive-laden gas stream to flow to the second handpiece when it is of same construction as the first handpiece. Finally, a foot pedal is provided for the operator to control the flow of the pressurized gas stream by alternatively enabling and disabling its flow, whereby the selected handpiece may be provided with liquid and gas streams at the option of the operator.

These and other features, aspects and advantages of the present invention will become better understood with reference to the following drawings, description and claims. For a better understanding of the invention, its operating advantages and the specific objects attained by its uses, reference should be made to the accompanying drawings and descriptive matter in which there are illustrated preferred embodiments of the invention. The foregoing has outlined some of the more pertinent objects of the invention. These objects should be construed to be merely illustrative of some of the more prominent feature and applications of the present invention. Many other beneficial results can be attained by applying the disclosed invention in a different manner or by modifying the invention within the scope of the disclosure. Accordingly, other objects and a fuller understanding of the invention and the detailed description of the preferred embodiments in addition to the scope of the invention illustrated by the accompanying drawings.

BRIEF DESCRIPTION OF THE DRAWINGS

FIG. 2 is a cross section of the head and nozzle taken from the handpiece shown in FIG. 1.

FIG. 3 is an axially oriented end view of the servicing end of the handpiece as seen from a distal vantage point, highlighting the topography of the nozzle on the head.

FIG. 4 is a top view of the servicing end of the handpiece highlighting the tubing platform.

FIG. 5 shows a block diagram of the invention as it is configured for two handpieces.

DETAILED DESCRIPTION OF THE INVENTION

Figure 1:
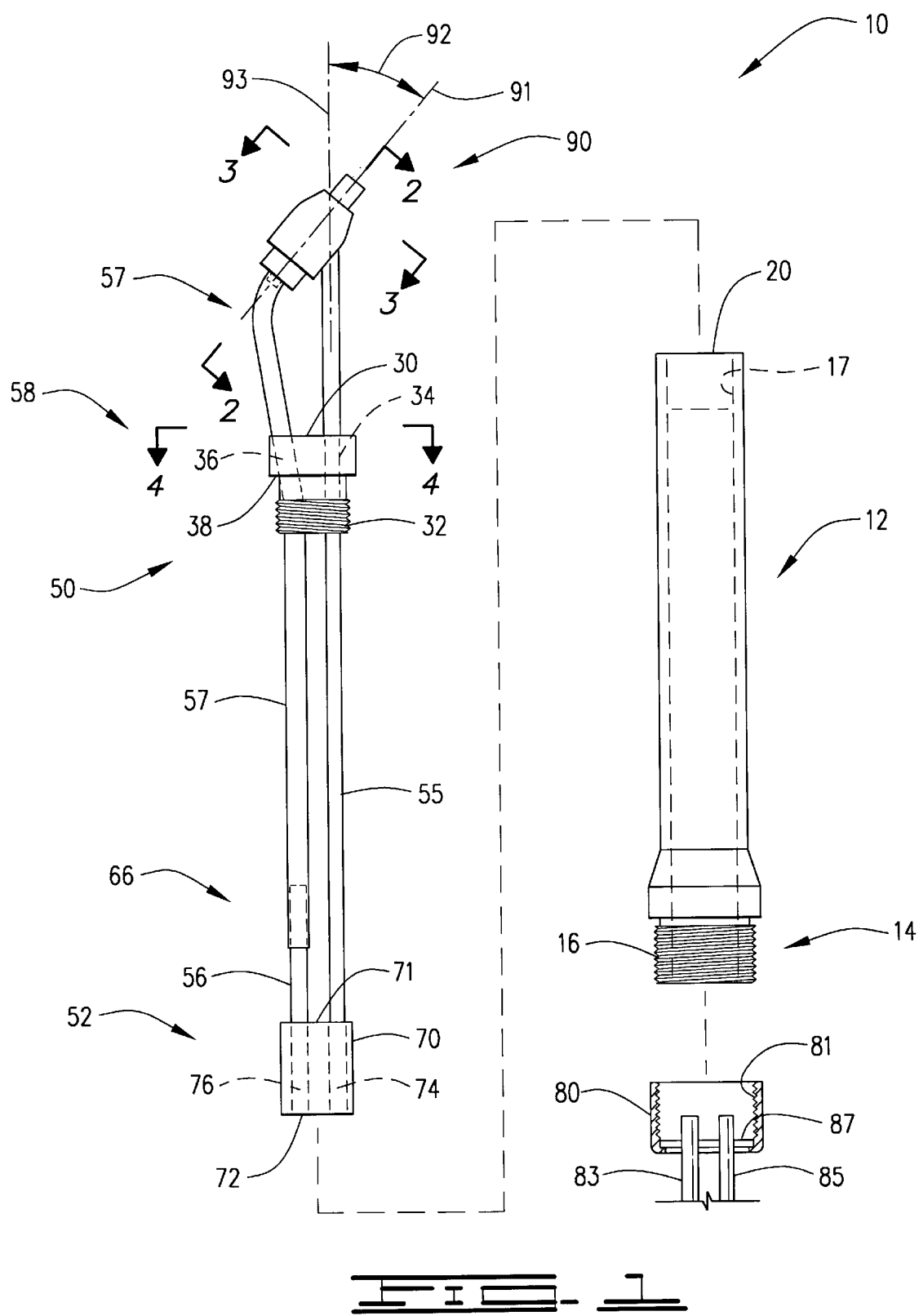
FIG. 1 is a side view of a handpiece and an extruded jacket.

The following detailed description shows the best currently contemplated modes of carrying out the invention. The description is not to be taken in a limiting sense, but is made for the purpose of illustrating the general principles of the invention and the best mode for practicing the invention, since the scope of the invention is best defined by the appended claims.

An embodiment of a dental abrasion system according to the invention is shown in FIG. 5. The system is portable and self contained, and requires no external power source. It may therefore be used in areas without commercial power, such as third world countries, open fields, jungles, ocean-going vessels, and the like. It is configured to conveniently deliver streams of abrasive-laden gas and liquid to the mouth area so that various dental operations may be performed. Sufficient force for generating pressurized streams of abrasive-laden gas or liquid is provided by a source of pressurized gas, preferably a tank of nitrogen, $N_2$, having a approximate pressure of 200 psi. The capacity of the tank may be chosen to promote portability and duration of the operation, and it is thus dependent upon the particular application. The system has the two primary functions of cleaning teeth and of abrading, or cutting, dental material in preparation for insertion of fillings. It also provides a rinsing function for maintaining visibility and cleanliness of the tooth area being operated upon and a drying function for removing moisture in the tooth area that might impede operations. While the system may used for dental purposes, it may also be used in any application in which it is desired to remove a overlaying material from a hard surface without damaging the underlaying surface or to remove portions of a hard surface.

Separate means are provided for the cleaning function and the abrading function. The cleaning function is provided by a handpiece that delivers a pressurized, abrasive-laden gas stream to the tooth area, simultaneously with a parallel, pressurized liquid stream, which will be presently described in greater detail. The liquid stream is directed to the same area of the tooth to which the abrasive-laden gas stream is also directed, in order to reduce the plume of dust and debris so that it does not impede breathing or visibility of the tooth area. The abrasive material and gas pressure are chosen to prevent undue wear of the tooth enamel while removing any coatings of calculus or plaque. The abrasive material is preferably a water soluble abrasive such as sodium bicarbonate, but other water soluble abrasives may be used without departing from the scope of the invention, as for example, sodium glutamate, sodium gluconate, or potassium bicarbonate.

The abrading, or cutting, function is provided by a handpiece identical in construction to the handpiece provided for the cleaning function. This duplication of design promotes interchangeability, manufacturability, and reduction in inventory part count. It permits the overall system to continue to be used when one of the functions is impaired and nonfunctional. Like the cleaning handpiece, the abrading handpiece delivers a pressurized, abrasive-laden gas stream to the tooth area simultaneously with a pressurized liquid stream to the same area. The abrasive material and gas pressure are chosen to abrade tooth at a reasonable rate, so that the size and depth of the tooth area being abraded can be easily controlled by an operator skilled in the use of the system. The abrasive material is preferably a water insoluble abrasive in powdered form such as aluminum oxide, $Al_2O_3$, although other water insoluble abrasives may be used without departing from the scope of the invention.

The cleaning function and the abrading function each has its own separate abrasive mixing device for entraining the associated abrasive material in the pressurized gas. Such abrasive mixing devices are commonly known to the art and may typically be of a type shown in U.S. Pat. No. 3,972,123, to Black, incorporated herein by reference. Each abrasive material is contained in its own separate reservoir that associated with the particular handpiece.

An embodiment of the handpiece used with the invention is shown in FIG. 1, and generally referenced as handpiece 10. Handpiece 10 is shown with its outer jacket removed to better illustrate the construction of the invention. The handle assembly of handpiece 10 comprises a feeding tube assembly 50 and jacket 12. Feeding tube assembly 50 is inserted into jacket 12 as shown and secured by engaging the external threads 32 of feeding tube assembly 50 with the internal threads 17 of the jacket 12 in rotational maneuver, so that they may be easily disassembled for autoclaving or replacement of parts.

At the input end 52 of feeding tube assembly 50 is a cylindrical plug 70 having a liquid inlet 74 and a gas inlet 76 bored therethrough parallel to its sides and perpendicular to its top 71 and bottom 72 surfaces, for removable connection to external sources of liquid and gas, respectively. A linear gas tube 56 may be force fitted into gas inlet 76 a short distance. A curved gas tube 57 may be connected to the upper end 66 of linear gas tube 56 to extend through the oblique channel 36 in cap 30 in a gentle curve 67 to terminate at the head assembly 90. A rigid water tube 55 may be force fitted into the liquid inlet 74 and extends in a straight line through the water channel 34 in cap 30 to terminate in a slot also in head assembly 90 to provide a rigid platform for the head assembly 90. Cap 30 and cylindrical plug 70 are maintained in a spaced relationship by their fixed connection with rigid water tube 55.

The cap 30 has external threads 32 for cooperative attachment with internal threads 17 of jacket 12, so that, when feeding tube assembly 50 is inserted into sleeve 12 and threads 32 are rotatingly engaged with threads 17 until lip 38 abuts the top edge 20 of jacket 12, the bottom surface of cylindrical plug 70 is flush with or slightly extending beyond the plane of the bottom end of sleeve 12. A fitting 80 is provided to mate the water line 85 and the gas line 83 with the liquid inlet 74 and the gas inlet 76, respectively. Internal threads 81 in fitting 80 are provided for cooperative attachment with external threads 16 on the bottom end 14 of jacket 12, so that, when the water and gas lines 85, 83 are inserted into the water and gas inlets 74, 76, gasket 87 is brought into snug abutment with the bottom surface 72 of cylindrical plug 70 for sealing the pressurized lines. Threads 16, 81 are right-handed and threads 17, 32 are left-handed, so that when threads 16, 81 are tightened, any torque applied to feeding tube assembly 50 tends to also tighten threads 17, 32.

Because of the wearing effect of the abrasive on the internal surfaces of the gas tubes, long term use of the abrasives requires either frequent maintenance and replacement or materials of special construction. The linear gas tube 56 may be substantially linear so that the gas stream flows parallel to its sides and does not appreciably abrade its inner surface. Stainless steel is the preferable material for linear gas tube 56 since it provides durability and rigidity and since it can be autoclaved. The curved gas tube 57 may be constructed from different autoclavable materials, such as selected plastics such as polypropylene, carbide or other ceramic materials, or other materials suitable and well known in the arts for withstanding the autoclave heating level, with polypropylene being preferred for its flexibility. Selected plastics have been observed to possess the unexpected benefit of abrading more slowly and thus lasting longer than harder materials, especially when the abrasive is aluminum oxide. Although this phenomenon is not completely understood, it is believed to result from the resiliency of the selected plastics being able to withstand long term bombardment by abrasive particles. Furthermore, selected plastics, when incorporated in curved areas of the gas passage where higher abrasion rates are observed to occur, may be easily replaced, resulting in less maintenance and refurbishment expense.

The head assembly 90 (FIG. 1) is configured to direct streams of pressurized liquid, preferably water, and abrasive-laden, pressurized gas to the same selected tooth area so that the streams do not intentionally meet yet may combine at the selected tooth area. The streams are preferably parallel and not converging. As will be presently seen, the unique design of the head assembly 90 ensures that the exit openings for the streams of pressurized liquid and abrasive are separated and do not promote clogging of the abrasive passage. Head assembly 90 is supported on an end of rigid water tube 55 at head angle 92. It comprises a head 94 with an axial bore 96 and a nozzle 98 inserted through and force fitted in the axial bore 96. Nozzle 98 and axial bore 96 are oriented about head centerline 91. The nozzle 98 has a length so that so that the exit end 101 and the entry end 99 each protrude a distance from the head 94. Entry end 99 of nozzle 98 is surrounded by a plastic collar 95. An end of the curved gas tube 57 terminates at the entry end 99 where it is inserted over and around entry end 99 to form a connection that resists disengagement by the pressure in curved gas tube 57. A gas channel is thus formed by linear gas tube 56, curved gas tube 57, and nozzle 98. The nozzle 90 may be constructed of a suitable material to withstand the abrasive action of the abrasive-laden pressurized gas that emanates therefrom; such materials may include carbide, drilled sapphire, or stainless steel.

The rigid water tube 55 delivers pressurized water to the head assembly 90. The head 94 is supported by rigid water tube 55 being inserted into an angled hole drilled into the side of head 94 and then secured to head 94 by means of spot welding, braising, or other methods well known in the art. The angled hole is formed so that the head is angled 40° above the horizontal, i.e. so that angle 92 between the tube centerline 93 and the head centerline 91 is generally oriented at a 50° angle, to further prevent excessive abrading of the inner surface of the curved gas tube 57. A water passage 97 is drilled parallel to head centerline 91, forming an off-center passage from the rigid water tube 55 to the water orifice 100 (FIGS. 2, 3) and placing the rigid water tube 55 in communication with the external environment. The water orifice 100 is separated a distance from the exit end 101 of nozzle 98 as it protrudes from head 94 to prevent possible clogging of the water passage by stray abrasive.

In operation, the abrasive-laden gas stream may be pressurized by normal air, carbon dioxide, nitrogen, or other suitable gases, with dry gasses such as nitrogen being preferable since they contain little or no moisture which might combine with the abrasive to clog nozzle 90. The abrasive is known to excessively wear the feed tubes where they change direction, so that they must be frequently replaced. It has been found that keeping the path substantially straight will extend the operational life of such feed tubes. Maintaining a head angled 50° above the horizontal, i.e. at a head angle 92 of 40°, allows the path of curved gas tube 57 to remain essentially straight with only a gentle curve at 67, while allowing the apparatus 10 to be used in a hand position that is comfortable for the user. Furthermore, the use of resilient plastics has been observed to possess the unexpected benefit of abrading more slowly than harder, more resistant materials, and thus lasts longer.

Referring to FIG. 5, the abrasion handpiece 10 is connected with a mobile abrasion system 500 containing more than one type of abrasion handpiece. The system may support a water soluble abrasion handpiece 510 suitable for cleaning and gentle abrading with a water soluble abrasive such as sodium bicarbonate. The system may also support a separate water insoluble abrasion handpiece 520 suitable for deep abrading and cutting to remove dental material. The water insoluble abrasion handpiece 520 utilizes high pressure and a water insoluble abrasive such as aluminum oxide.

A user of the system may toggle use between the water soluble abrasion handpiece 510 and the water insoluble abrasion handpiece 520 with switch 530. The switch 530 restricts a 200 psi flow of gas to either the water soluble abrasive handpiece 510 or the water insoluble abrasive handpiece 520. Switch 530 directs the flow of pressurized gas to flow lines 540, 560, associated with the water insoluble abrasion handpiece 520, and to flow lines 550, 570, associated with the water soluble abrasion handpiece 510. A third handpiece, a syringe 610, is also provided as a convenience to the user for drying the tooth area of moisture and rinsing the tooth area of foreign matter.

A nitrogen tank 650 provides pressurized nitrogen gas to enable all components of the system. Nitrogen gas at a pressure of approximately 200 psi leaves nitrogen tank 650 through flow line 651 where it is divided into two streams by T-fitting 653. One stream flows through flow line 655 to a foot pedal 640 which allows the user to manually engage up to the full amount of 200 psi by depressing the foot pedal 640. The other stream flows through flow line 657 to air regulator 659. The air regulator 659 restricts the pressure off the gas to 35 psi and sends it either through flow line 661 directly to the syringe 610 where its flow is manually controlled from syringe 610 or through flow line 663 to the water bottle 620. The water bottle 620 is thus maintained at a generally constant pressure of 35 psi so that the pressure of the water leaving the water bottle 620 is also 35 psi. Water leaving water bottle 620 flows either through flow line 665 directly to syringe 610 where it is controlled manually from syringe 610 or through flow line 667 for use in either handpiece 510 or handpiece 520, in a manner which shall be presently described.

Turning attention to foot pedal 640, pressurized gas at 200 psi is controlled by manual foot pressure on foot pedal 640. When foot pedal 640 is depressed, pressurized gas is directed through flow line 656 to switch 530 which allows the user to manually select either handpiece 510 or handpiece 520 for operation.

When switch 530 is positioned to select handpiece 520, pressurized gas is directed through flow lines 540, 560 whenever foot pedal 640 is depressed. Pressurized gas in flow line 540 enters an entraining reservoir 575 containing an abrasive material such as aluminum oxide appropriate for harsh abrading and cutting dental material. The infusion means by which the pressurized gas in flow line 540 becomes entrained by the aluminum oxide powder is well-known to the art, as shown, for example, in U.S. Pat. No. 3,972,123, issued to Black, and incorporated herein by reference; other similar infusion means may be used without departing from the scope or intent of the invention. The entrained gas then continues from entraining reservoir 575 through flow line 541 to the gas line 83 (FIG. 1) associated with handpiece 520. Simultaneously, pressurized gas in flow line 560 is directed to water control valve 590 to allow water to flow from water bottle 620 at a water pressure of 35 psi. The water is further restricted by regulator valve 593 to a pressure of 15 psi and thence directed through flow line 594 to water line 85 (FIG. 1) associated with handpiece 520.

In a similar manner, when switch 530 is positioned to select handpiece 510, pressurized gas is directed through flow lines 550, 570 whenever foot pedal 640 is depressed. Pressurized gas at 200 psi in flow line 550 is restricted to a pressure of 100 psi by air regulator 552. It then flows through flow line 553 to enter an entraining reservoir 576 containing a water soluble abrasive material such as sodium bicarbonate powder appropriate for cleaning and gentle abrading without removal of tooth enamel. The pressurized gas becomes entrained with the sodium bicarbonate powder and continues from entraining reservoir 576 through flow line 554 to the gas line 83 (FIG. 1) associated with handpiece 510. Simultaneously, pressurized gas in flow line 570 is directed to water control valve 595 to allow water to flow from water bottle 620 at a water pressure of 35 psi. The water is further restricted by regulator valve 596 to a pressure of 15 psi and thence directed through flow line 597 to water line 85 (FIG. 1) associated with handpiece 510.

In another embodiment, the system shown in FIG. 5 can be configured for use in equine dentistry. In such applications, the system may be configured for easy portability by reducing the size of the tanks and assembling the components of the system into a compact, portable arrangement. Further modifications are necessary for convenient use for equine dentistry. The length of the jacket 12 and feeding tube assembly 50 (shown in FIG. 1) is extended to about 13.5 inches so that the handpiece 10, when be inserted into the mouth of a horse, can reach the rearward teeth. Optionally, in some embodiments of the apparatus, the entraining reservoir 575 is bypassed or eliminated, and the handpiece 520 is replaced by a standard dentist's drill driven by high pressure gas and adapted for use with the elongate feeding tube assembly. In this manner, a standard dentists drill may be used to perform equine dentistry. Additionally, the angle above the horizontal for either handpiece 520 or the dentist's drill is set to approximately 25°, i.e. head angle 92 is set to 65°, instead of 40°, for comfortable access to rear portions of the horse's mouth.

As has been demonstrated, the present invention provides advantageous systems and methods incorporating a novel handpiece, multiple handpieces in a mobile system, and a handpiece suitable for use in equine dentistry. While the preferred embodiments of the present invention have been described, additional variations and modifications in those embodiments may occur to those skilled in the art once they learn of the basic inventive concepts. Therefore, it is intended that the appended claims shall be construed to include both the preferred embodiment and all such variations and modifications as fall within the spirit and scope of the invention.

I claim:

1. A handpiece for directing a pressurized abrasive-laden gas stream and a pressurized liquid stream as separate streams to a work area, the handpiece comprising:

a elongate handle having a handle centerline, the handle sized to gripped by a hand of a person, the handle having a first end and a second end;

a head assembly for attachment to the first end, the head assembly having a head centerline, the head assembly having a nozzle protruding a distance from the head assembly, the nozzle directing the abrasive-laden gas stream emanating from a tip of the nozzle to the work area, the head assembly also having an orifice directing the pressurized liquid stream to the work area;

a gas channel receiving the pressurized abrasive-laden gas stream at the second end and directing the pressurized abrasive-laden gas stream through the handle and the head assembly to exit the nozzle, the gas channel having a linear portion comprised of a hard durable material and a curved portion comprised of a flexible material; and a liquid channel receiving the pressurized liquid stream at the second end and directing the pressurized liquid stream through the handle and head assembly to exit the orifice, wherein the gas channel is not confined by the liquid channel and the liquid channel is not confined by the gas channel.

2. The handpiece described in claim 1, wherein the curved portion comprised of polypropylene.

3. The handpiece described in claim 1, wherein an angle between the handle centerline and the head centerline is in the range of 40° to 70°.

4. The handpiece described in claim 3, wherein the angle is 50°.

5. The handpiece described in claim 3, wherein the angle is 65° and the handle has a length greater than 12", whereby the handpiece may be used within a mouth of a horse to reach the rearward teeth.

6. The handpiece described in claim 1, wherein the head assembly is externally threaded and the handle is internally threaded, the head assembly removably attached to the handle by a clockwise rotation of the head assembly with respect to the handle from the viewpoint of the second end.

7. An abrasion system for abrading a work area, the system comprising
- a pressurized gas stream;
- a pressurized liquid stream, the pressurized liquid stream provided by a tank of water pressurized by the pressurized gas stream;
- a means for entraining a first abrasive material in the pressurized gas stream to produce an first abrasive-laden gas stream;
- a first handpiece simultaneously directing the first abrasive-laden gas stream and the pressurized liquid stream to the work area, whereby the pressurized liquid stream reduces the resulting plume of material emanating from the work area resulting from the first abrasive-laden gas stream; and
- a second handpiece.

8. The abrasion system described in claim 7, wherein the second handpiece receives the pressurized gas stream to operate a dentist's drill and directs the pressurized liquid stream to the work area.

9. The abrasion system described in claim 7, further comprising
- a means for entraining a second abrasive material in the pressurized gas stream to produce a second abrasive-laden gas stream; and
- the second handpiece simultaneously directing the second abrasive-laden gas stream and the pressurized liquid stream to a work area, whereby the pressurized liquid stream reduces the resulting plume of material emanating from the work area resulting from the second abrasive-laden gas stream.

10. The abrasion system described in claim 9, wherein the first abrasive material is non-soluble.

11. The abrasion system described in claim 10, wherein the first abrasive material is aluminum oxide ($Al_2O_3$).

12. The abrasion system described in claim 9, wherein the first abrasive material is soluble.

13. The abrasion system described in claim 12, wherein the first abrasive material is sodium bicarbonate ($NaHCO_3$).

14. The abrasion system described in claim 7, wherein the first abrasive material is non-soluble.

15. The abrasion system described in claim 14, wherein the first abrasive material is aluminum oxide ($Al_2O_3$).

16. The abrasion system described in claim 7, wherein the first abrasive material is soluble.

17. The abrasion system described in claim 16, wherein the first abrasive material is sodium bicarbonate ($NaHCO_3$).

18. The abrasion system described in claim 7, further comprising a means for selecting one of the handpieces for operation.

19. The abrasion system described in claim 7, wherein the pressurized gas stream is provided by a tank containing gas under pressure.

20. The abrasion system described in claim 7, wherein the gas is nitrogen gas.

21. A mobile abrasion system comprising
- a gas tank providing a pressurized gas stream comprised of nitrogen gas;
- a water tank providing a pressurized liquid stream, the water tank receiving pressure from the pressurized gas stream;
- a first reservoir containing a first abrasive material, the first reservoir receiving the pressurized gas stream, entraining the first abrasive material within the pressurized gas stream, and providing a first abrasive-laden gas stream;
- a first handpiece receiving the first abrasive-laden gas stream and the pressurized liquid stream;
- a second handpiece receiving the pressurized liquid stream;
- a switch alternatively enabling the first abrasive-laden gas stream and the pressurized liquid stream to flow to the first handpiece and enabling the pressurized liquid stream to flow to the second handpiece, wherein the nonselected handpiece is disabled from the streams; and
- a foot pedal alternatively enabling the flow of the pressurized gas stream and disabling the flow of the pressurized gas stream, whereby the selected handpiece may be provided with liquid and gas streams at the option of the operator.

22. The mobile abrasion system described in claim 21, wherein the second handpiece is a dentist's drill.

23. The mobile abrasion system described in claim 21, further comprising a second reservoir containing a second abrasive material, the second reservoir receiving the pressurized gas stream, entraining the second abrasive material within the pressurized gas stream, and providing a second abrasive-laden gas stream, wherein the second handpiece receives the second abrasive-laden gas stream along with the pressurized liquid stream and the switch enables the second abrasive-laden gas stream to flow to the second handpiece along with the pressurized liquid stream when the second handpiece is selected.

* * * * *